United States Patent [19]

Kuroda

[11] Patent Number: 4,984,415
[45] Date of Patent: Jan. 15, 1991

[54] METHOD AND APPARATUS FOR BLOCKADING AN OPENING THROUGH A CYLINDRICAL MOUTHPIECE OF A SYNTHETIC RESIN CONTAINER

[75] Inventor: Nihee Kuroda, Osaka, Japan
[73] Assignee: Fuso Pharmaceutical Industries, Ltd., Osaka, Japan
[21] Appl. No.: 296,668
[22] Filed: Feb. 13, 1989

Related U.S. Application Data

[62] Division of Ser. No. 178,342, Apr. 6, 1988, abandoned.

[30] Foreign Application Priority Data

Apr. 7, 1987 [JP] Japan .................................. 62-85332
Nov. 11, 1987 [JP] Japan ................................ 62-284973

[51] Int. Cl.⁵ .......................... B67B 1/04; B67B 1/08; B65B 7/28; B65B 51/10
[52] U.S. Cl. ........................................ 53/478; 53/486; 53/489; 156/69
[58] Field of Search ................ 53/478, 486, 489, 373, 53/379; 215/247; 156/69

[56] References Cited

U.S. PATENT DOCUMENTS

| | | |
|---|---|---|
| 2,710,986 | 6/1955 | Gray .................................. 156/69 X |
| 2,783,908 | 3/1957 | Winfield .............................. 215/247 |
| 2,922,832 | 1/1960 | Gottschall et al. ................ 53/478 X |
| 2,989,785 | 6/1961 | Stahl .................................. 156/69 X |
| 3,707,274 | 12/1972 | Hausler et al. ......................... 53/486 |
| 3,824,138 | 7/1974 | Karobath et al. ..................... 156/69 |
| 3,972,758 | 8/1976 | Bieber .................................. 53/486 X |
| 4,046,610 | 9/1977 | Lilja ................................... 53/478 X |
| 4,074,619 | 2/1978 | Feliks ................................ 156/69 X |
| 4,219,912 | 9/1980 | Adams .............................. 215/247 X |
| 4,254,884 | 3/1981 | Maruyama ....................... 215/247 X |
| 4,294,249 | 10/1981 | Sheehan et al. ................. 215/247 X |
| 4,307,766 | 12/1981 | Tanokura ......................... 215/247 X |
| 4,430,142 | 2/1984 | Ochi et al. ........................ 53/478 X |
| 4,554,125 | 11/1985 | Knapp ............................. 215/247 X |
| 4,785,992 | 11/1988 | Goeppner ........................ 156/69 X |

Primary Examiner—Horace M. Culver
Attorney, Agent, or Firm—Wenderoth, Lind & Ponack

[57] ABSTRACT

There is disclosed a simply constructed apparatus for and a ready method of blockading a mouthpiece of a transfusion synthetic resin container used for medical drip infusion. Based on the apparatus and the method thereof, insertion of an instillation needle can be facilitated, and there is no leakage of fluid. Besides, low costs of manufacture suffice, and high efficiency can be attained.

5 Claims, 2 Drawing Sheets

METHOD AND APPARATUS FOR BLOCKADING AN OPENING THROUGH A CYLINDRICAL MOUTHPIECE OF A SYNTHETIC RESIN CONTAINER

This is a Rule 1.60 divisional application of Ser. No. 178,342, filed Apr. 6, 1988, now abandoned.

BACKGROUND OF THE INVENTION

1. Field of the Invention

The present invention relates to a simple apparatus for and a method of blockading a mouthpiece of a transfusion synthetic resin container designed for medical drip infusion, in which insertion of an insillation needle can be facilitated and there is no possibility of leakage of fluid.

2. Description of the Prior Art

Conventional means for blockading the mouthpiece of the synthetic resin container is typically arranged in three ways. Firstly, after a tight-sealing stopper has been welded to the mouthpiece of the synthetic resin container, a leakage prevention rubber stopper is covered thereon. Secondly, the synthetic resin stopper and the leakage prevention rubber stopper are previously fitted to the mouthpiece of the synthetic resin container. Thirdly, the synthetic resin stopper and the leakage prevention rubber stopper are formed before-hand into one united body, and this united body is welded to the mouthpiece of the container. These constructions are all complicated and have difficulty of operation. Besides, such constructions are relatively costly and are inefficient for preventing the leakage.

SUMMARY OF THE INVENTION

It is a primary object of the present invention to provide means for simplifying both a constitution and steps of manufacture and yielding a remarkable effect in preventing the leakage, the arrangement being such that a leakage prevention rubber stopper is fitted in a mouthpiece of a synthetic resin container designed for transfusion and is further press-welded thereto by heating from above, and an upper portion of the mouthpiece is crookedly press-fitted in an outer peripheral portion of an upper surface of the rubber stopper to blockade the mouthpiece.

These and other objects, features and advantages of the invention will become more apparent on reading the following description with reference to the accompanying drawings.

BRIEF DESCRIPTION OF THE DRAWINGS

The accompanying drawings in combination illustrate embodiments of the present invention.

FIG. 1 is a perspective view illustrating parts before effecting tight-sealing;

FIG. 2 is a sectional view depicting a state in which a rubber stopper is inserted into a mouthpiece of a bottle;

FIG. 3 is a sectional view showing press-heating steps;

FIG. 4 is a perspective view of parts before effecting the tight-sealing;

FIG. 5 is a sectional view illustrating a situation just before performing the press-heating steps after fitting the rubber stopper in the mouthpiece of the bottle; and FIG. 6 is a sectional view illustrating a state of completing a blockading process.

DETAILED DESCRIPTION OF THE PREFERRED EMBODIMENTS

Figure 1:
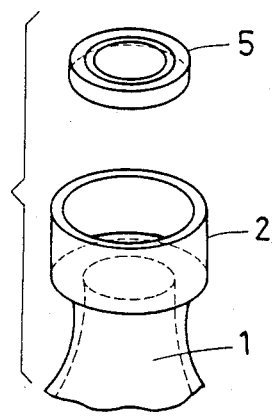
FIGS. 1 through 3 illustrate a first embodiment.

The embodiments of the present invention will hereinafter be described with reference to the accompanying drawings.

Embodiment 1

The reference numeral 1 designates a transfusion synthetic resin container having thermoplasticity, and the numeral 2 represents a mouthpiece formed by slightly expanding a top portion (a bottom portion when performing the transfusion) of the container 1. The numeral 5 denotes a disk-like rubber stopper for tightly sealing the mouthpiece 2 of the container 1, this stopper 5 being so recessed as to be fittable in the mouthpiece 2. The numeral 6 represents a metallic cap for forming the mouthpiece, the inner surface of which is coated with Teflon 10 to prevent adhesion of fused synthetic resin.

Figure 2:
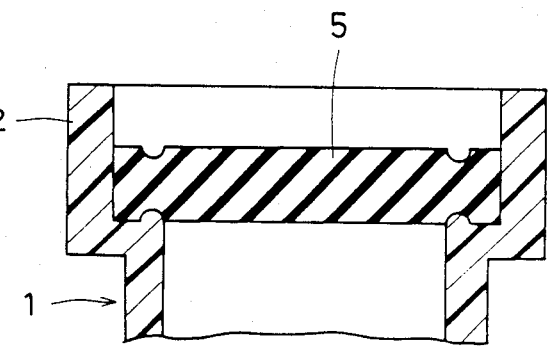
Figure 3:
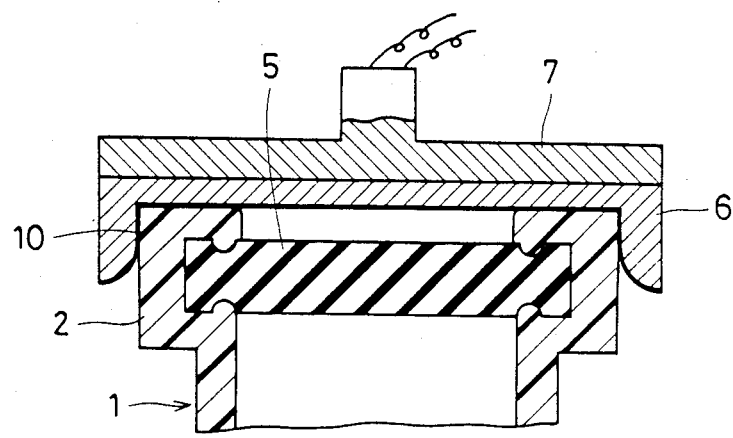
Figure 4:
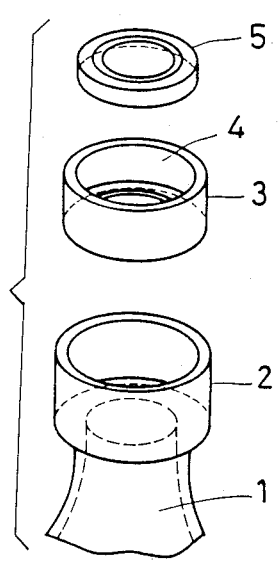
FIGS. 4 through 6 illustrate a second embodiment.

The rubber stopper 5 is thus, as illustrated in FIG. 2, fitted in the mouthpiece 2 from above, and the mouthpiece forming metallic cap 6 is covered on the mouthpiece 2 of the containter 1 from above. Subsequently, a welding heater 7 is heat-pressed on the upper surface of the metallic cap 6, with the result that the mouthpiece 2 is, as depicted in FIG. 3, crooked inwards. Then, the rubber stopper 5 is integrally fixed to the inside of the mouthpiece 2. Note that if the rubber stopper is coated with the same material as that of the container, great adhesivity is required for providing the effectiveness, and hence the rubber stopper should arbitrarily be used when being put into practice.

In accordance with the present invention having the above-described construction, the rubber stopper 5 is integrally fixed to the mouthpiece and this facilitates the manufacture with high efficiency. The apparatus and the method according to the present invention requires less amount of costs. Moreover, the blockaded portion is tightly sealed and hence there is no axiety for leakage.

Embodiment 2

Figure 5:
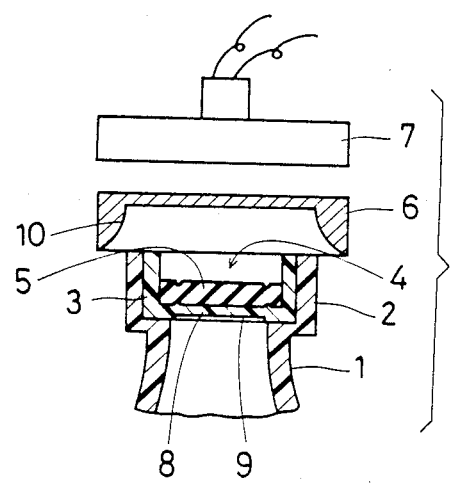
Figure 6:
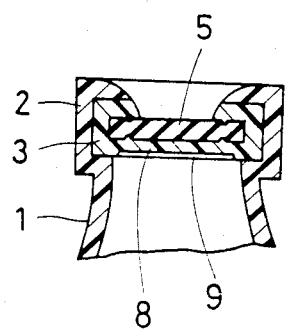

The numeral 1 designates a transfusion synthetic resin container having thermoplasticity, and the numeral 2 stands for a mouthpiece formed by slightly expanding a top portion (a bottom portion when effecting transfusion) of the container 1. The numeral 3 denotes a synthetic resin mouthpiece stopper for sealing the mouthpiece 2 of the container 1, this stopper 3 being likewise formed of the same synthetic resin having the thermoplasticity as that of the container 1. The cylindrical mouthpiece stopper 3 fittable in the mouthpiece 2 is blockaded by a thin bottom plate 8, the central lower surface of which is formed with a needle insertion recess 9. The numeral 4 indicates an upper opening of the mouthpiece stopper 3. The numeral 5 denotes a rubber stopper fittable in the upper opening, this rubber stopper 5 assuming a disk-like configuration and functioning to prevent the leakage in practical use. The numeral 6 denotes a metallic cap for forming the mouthpiece, the inner surface of which is coated with Teflon 10 in order to prevent adhesion of the fused synthetic resin. As illustrated in FIG. 5, from the upper portion of the mouthpiece 2 of the container 1 in which the rubber stopper 5 is fitted in the upper opening 4 of the mouthpiece stopper 3, the mouthpiece forming metallic cap 6 is covered hereon, and welding heater 7 is pressed on the upper surface of the metallic cap 6. The mouthpiece 2 and the upper portion of the mouthpiece stopper 3 are welded so that they are crooked inwards form the outer periphery thereof. It is to be noted that because an insertion recess 9 is formed in the lower surface of a bottom portion 8 of the sealing mouthpiece stopper 3, the resistance produced when the needle penetrates the rubber stopper 5 and the mouthpiece stopper 3 decreases in the practical use, thereby causing no damage on the needle.

Although illustrative embodiments of the present invention have been described in detail with reference to the accompanying drawings, it is to be understood that the invention is not limited to those precise embodiments. Various changes or modifications may be effected therein by one skilled in the art without departing from the scope or spirit of the invention.

What is claimed is:

1. A method of blockading an opening through a cylindrical mouthpiece of a synthetic resin container, comprising the steps of:
    fitting a disk-shaped rubber stopper within the cylindrical mouthpiece of said synthetic resin container so as to blockade the opening thereof; and
    press-heating the cylindrical mouthpiece of the synthetic resin container against an upper portion of said disk-shaped rubber stopper by covering the mouthpiece of the synthetic resin container with a metallic mouthpiece forming cap having an inner surface coated with Teflon, and pressing a welding heater against an upper surface of said metallic mouthpiece forming cap, such that an upper portion of the cylindrical mouthpiece becomes integrally fixed about an entire circumference thereof to said upper portion of said disk-shaped rubber stopper, to thereby unite said disk-shaped rubber stopper and the cylindrical mouthpiece of the synthetic resin container as a single body.

2. A method of blockading an opening through a cylindrical mouthpiece of a synthetic resin container, comprising the steps of:
    fitting a cup-shaped synthetic resin mouthpiece stopper within the cylindrical mouthpiece of the synthetic resin container;
    fitting a disk-shaped rubber stopper within the cup-shaped synthetic resin mouthpiece stopper;
    press-heating the cylindrical mouthpiece of the synthetic resin container and the cup-shaped synthetic resin mouthpiece stopper, such that an upper portion of the cup-shaped synthetic resin mouthpiece stopper becomes integrally fixed about an entire circumference thereof to an upper portion of said disk-shaped rubber stopper, and such that an upper portion of the cylindrical mouthpiece of the synthetic resin container becomes integrally fixed about an entire circumference thereof to said entire circumference of said cup-shaped rubber stopper, to thereby unite said disk-shaped rubber stopper, said cup-shaped synthetic resin mouthpiece stopper and the cylindrical mouthpiece of the synthetic resin container as a single body.

3. A method as recited in claim 2, wherein
    the step of press-heating the cylindrical mouthpiece and the cup-shaped mouthpiece stopper, comprises
    covering the mouthpiece of the synthetic resin container with a metallic mouthpiece forming cup; and
    pressing a welding heater against an upper surface of said metallic mouthpiece forming cup.

4. A method as recited in claim 2, wherein
    the step of press-heating the cylindrical mouthpiece and the cup-shaped mouthpiece stopper, comprises
    covering the mouthpiece of the synthetic resin container with a metallic mouthpiece having an inner surface coated with Teflon; and
    pressing a welding heater against an upper surface of said metallic mouthpiece forming cup.

5. A method as recited in claim 2, wherein
    the step of fitting said cup-shaped synthetic resin mouthpiece stopper within the cylindrical mouthpiece of the synthetic resin container, comprises
    fitting a cup-shaped synthetic resin mouthpiece stopper, having a needle insertion recess in an underside thereof, within the cylindrical mouthpiece of the synthetic resin container.

* * * * *